United States Patent
Vija

(12) United States Patent (10) Patent No.: US 8,629,404 B2
Vija (45) Date of Patent: Jan. 14, 2014

(54) METHOD AND APPARATUS TO OPTIMIZE INJECTED DOSE AND SCAN TIME IN SPECT IMAGING

(75) Inventor: Alexander Hans Vija, Evanston, IL (US)

(73) Assignee: Siemens Medical Solutions USA, Inc., Malvern, PA (US)

(\*) Notice: Subject to any disclaimer, the term of this patent is extended or adjusted under 35 U.S.C. 154(b) by 318 days.

(21) Appl. No.: 13/188,014

(22) Filed: Jul. 21, 2011

(65) Prior Publication Data

US 2012/0018645 A1 Jan. 26, 2012

Related U.S. Application Data

(60) Provisional application No. 61/366,257, filed on Jul. 21, 2010.

(51) Int. Cl.
*G01T 1/161* (2006.01)

(52) U.S. Cl.
USPC .............. 250/362; 250/363.01; 250/363.02; 250/363.03; 250/363.04

(58) Field of Classification Search
USPC ................... 250/362, 363.01–363.04
See application file for complete search history.

(56) References Cited

U.S. PATENT DOCUMENTS

| | | | |
|---|---|---|---|
| 2009/0171183 A1* | 7/2009 | Narayanan et al. | 600/408 |
| 2010/0140483 A1* | 6/2010 | Rousso et al. | 250/362 |

\* cited by examiner

*Primary Examiner* — David Porta
*Assistant Examiner* — Gisselle Gutierrez
(74) *Attorney, Agent, or Firm* — Peter Kendall

(57) ABSTRACT

An apparatus and method are provided for optimizing an amount of radiation dose and acquisition time in cardiac Single Photon Emission Computed Tomography (SPECT) imaging. The apparatus and method include providing an organ, acquiring images of the organ at projected views. Then a projected view that projects the organ as an annulus is selected; a region of interest (ROI) is also selected in the projected view, wherein the ROI is in a lateral wall of the organ. An average count in the ROI is determined; and an image quality of a reconstructed image based on the average count is predicted.

20 Claims, 6 Drawing Sheets

COUNTS c AND RELATION TO DWELL TIME AND DOSE FOR IQSPECT

| COUNTS | Tc99m - DOSE (mCi) | | | | USE |
|---|---|---|---|---|---|
| | | 9s | 14s | 18s | |
| <4 | VERY LOW | <4 | <3 | <2 | |
| 5-10 | LOW | 4-11 | 3.5-7 | <3 | 1st |
| 10-20 | MEDIUM | 11-22 | 7-14 | 3-5.5 | 1st |
| >20 | HIGH | >22 | >14 | >5.5 | 1st OR 2nd |

ATTENUATION/SCATTER CORRECTED

| COUNTS | DOSE (mCi) | | | | |
|---|---|---|---|---|---|
| | 9s | 14s | 18s | SUBSETS | ITERATIONS |
| <4 | <4 | <3 | <2 | | |
| 5-10 | 4-11 | 3.5-7 | <3 | 2 | 20 |
| 10-20 | 11-22 | 7-14 | 3-5.5 | 1 | 15 |
| >20 | >22 | >14 | >5.5 | 1 | 15 |

UNCORRECTED AND GATED

| COUNTS | DOSE (mCi) | | | | |
|---|---|---|---|---|---|
| | 9s | 14s | 18s | SUBSETS | ITERATIONS |
| <4 | <4 | <3 | <2 | | |
| 5-10 | 4-11 | 3.5-7 | <3 | 1 | 30 | GATED
| 10-20 | 11-22 | 7-14 | 3-5.5 | 1 | 20 |
| >20 | >22 | >14 | >5.5 | 1 | 20 |

POST SMOOTH:3D GAUSSIAN FWHM: 13 mm

FIG. 6

METHOD AND APPARATUS TO OPTIMIZE INJECTED DOSE AND SCAN TIME IN SPECT IMAGING

CROSS-REFERENCE TO RELATED APPLICATIONS AND CLAIM FOR PRIORITY

This application claims priority under 35 U.S.C. §119(e) from copending U.S. Provisional Patent Application Ser. No. 61/366,257 filed Jul. 21, 2010, the entire contents of which are incorporated herein by reference.

BACKGROUND OF THE INVENTION

1. Field of the Invention

This invention generally pertains to systems and methods for performing medical imaging. More particularly, the present invention is directed to an apparatus and method for optimizing an injected dose and scan time in SPECT imaging.

2. Description of the Related Art

The medical imaging field is improving. For example, image quality has greatly improved from a few years ago. In some cases, the changes are dramatic. Images are very life like. This has come about due to improvements in medical equipment design such as collimators and in software such as the reconstruction software that reproduces the images.

However, external factors such as medical care reimbursement is pushing the medical imaging field to be efficient at a low cost. With the high cost of malpractice insurance, hospitals and the medical field have to find a balance. Low cost medical service cannot be provided if it puts a patient at risk because it will in turn put the hospital or medical provider at risk for a law suit. Thus, there is a need to balance the two.

Reducing the scan time can allow more patients to be scanned. Reducing the dose reduces the problem of radiation exposure to the patient as well as the problem of acquiring radioactive pharmaceuticals that may be in short supply.

However, there are established protocols or guidelines concerning the use of scans and doses. For example, there are protocols or guidelines that are established for performing myocardial perfusion single photon emission CT (MPS) medical imaging scaning. The American Society of Nuclear Cardiology has proposed guidelines in Hansen C L, Goldstein R A, Akinboboye O O, et al. ASNC Imaging Guidelines For Nuclear Cardiology Procedures. J Nucl Cardiol. 2007; 14(6):e39-60, the contents of which are incorporated herein. The document provides tables, charts, and parameters. It is extensive concerning different options available to a practitioner. However, it provides more of a "one size fits all" approach as compared to a customized approach. The approach provided is also complicated because it has so many options for a practitioner. It is easy to get overwhelmed.

A need exists to be able to provide practical methods that can guide a user to plan a scan within a performance envelope to ensure useable image quality.

A need exists for adapting a scan time based on the patient to ensure the scan remains within a performance envelope.

A need also exists for a clinical protocol that is simple and uses a minimum number of parameters but still provides high quality images.

A further need exists for a system and method that reduces radiation doses to the patient and optimizes a scan time given a certain dose and a specific patient.

SUMMARY OF THE INVENTION

In accordance with the foregoing and other objects, an embodiment of the present invention provides an apparatus and method for optimizing an injected dose and scan time in a single photon emission computed tomography (SPECT).

According to one embodiment of the present invention, an apparatus and method is provided for simplifying the steps in a clinical protocol and uses a minimum number of parameters but still provides high quality images.

According to another embodiment of the present invention, an apparatus and method is provided for reducing radiation dose to a patient.

According to still another embodiment of the present invention, an apparatus and method is provided for adapting a scan time based on the patient to ensure the scan remains within the performance envelope.

An apparatus and method are provided for optimizing an amount of radiation dose and acquisition time in cardiac Single Photon Emission Computed Tomography (SPECT) imaging. The apparatus and method include providing an organ, acquiring images of the organ at projected views. Then a projected view that projects the organ as an annulus is selected; a region of interest (ROI) is also selected in the projected view, wherein the ROI is in a lateral wall of the organ. An average count in the ROI is determined; and an image quality of a reconstructed image based on the average count is predicted.

With these and other objects, advantages and features of the invention that may become hereinafter apparent, the nature of the invention may be more clearly understood by reference to the following detailed description of the invention, the appended claims, and the drawings attached hereto.

BRIEF DESCRIPTION OF THE DRAWINGS

The invention will be described in detail with reference to the following drawings, in which like features are represented by common reference numbers and in which:

FIG. 6 are tables showing regimes for counts in a lateral wall correlated to image quality in accordance with an embodiment of the present invention.

DETAILED DESCRIPTION OF THE PREFERRED EMBODIMENTS

Figure 1:
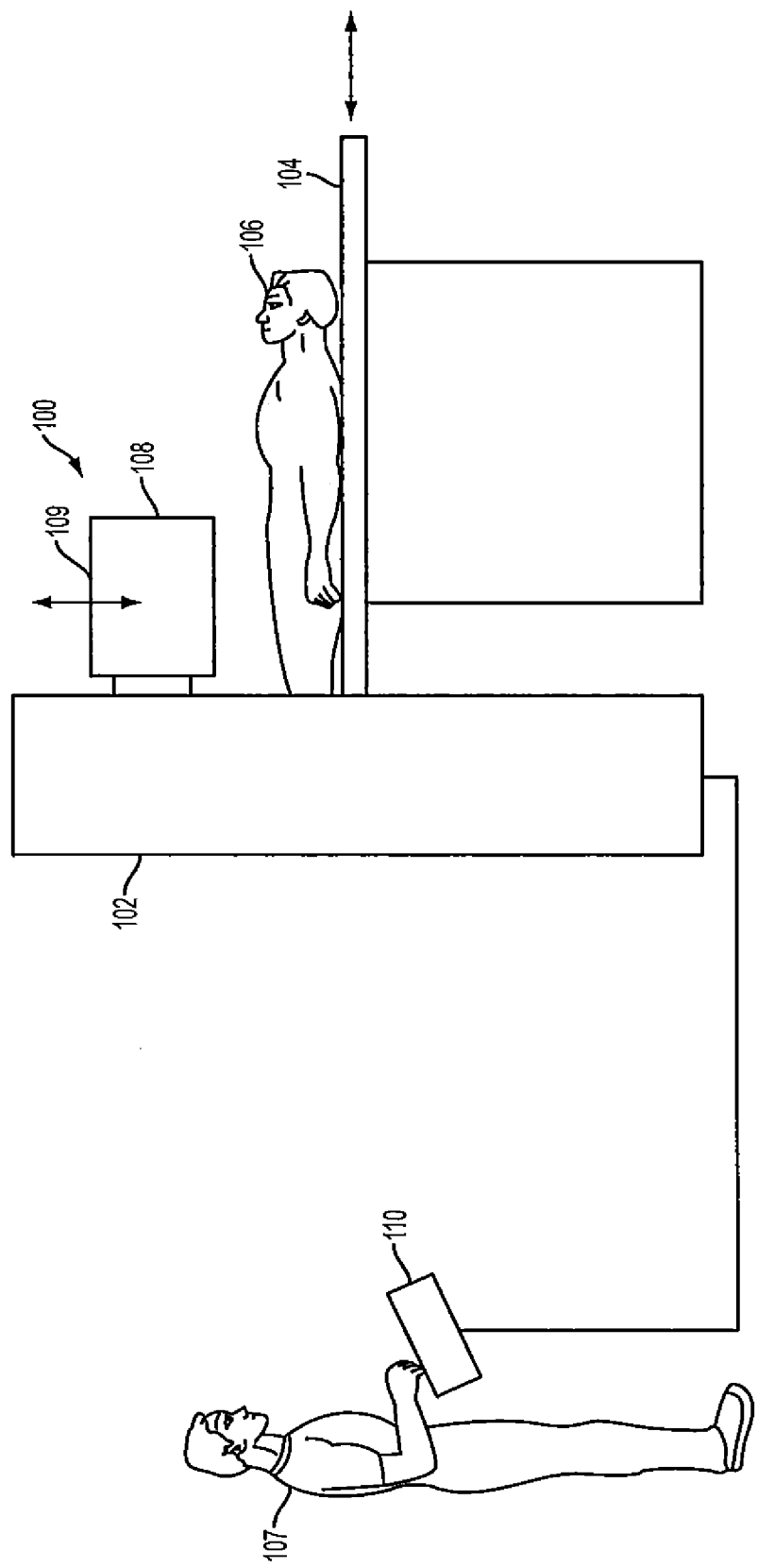
FIG. 1 is a diagram illustrating an exemplary medical imaging device in accordance with an embodiment of the present invention.

FIG. 1 depicts components of a SPECT system 100 (i.e., having a gamma or scintillation camera) which includes a gantry 102 supporting one or more detectors 108 enclosed within a metal housing and movably supported proximate a patient 106 located on a patient support (e.g., pallet or table) 104. The detectors are proximate collimators 109. The collimators a parallel beam, fan beam, multifocal collimator and the like. Typically, the positions of the detectors 108 can be changed to a variety of orientations to obtain images of a patient's body from various angles and locations along the patient's body. In many instances, a data acquisition console 110 (e.g., with a user interface and/or display) is located proximate a patient during use for a technologist 107 to manipulate during data acquisition. In addition to the data acquisition console 110, images are often "reconstructed" or developed from the acquired image data ("projection data") via a processing computer system that is operated at another image processing computer console including, e.g., an operator interface and a display, which may often be located in another room, to develop images. By way of example, the image acquisition data may, in some instances, be transmitted to the processing computer system after acquisition using the acquisition console.

To acquire SPECT images, the gamma camera is rotated around the patient on a gantry. Projections are acquired at defined points during the rotation, typically every 3-6 degrees. In most cases, a full 360 degree rotation is used to obtain an optimal reconstruction. The time taken to obtain each projection is also variable For example with Siemens IQ SPECT the time is minimal since the system uses a "sweet spot" based imaging technology where the organ of interest is always within view of the camera. Groups of projections are taken successively as the patient 106 on the table 104 is moved incrementally through the gantry 102 through the region of the patient 106 to be imaged. This gives a variable scan time 3 to 15 minutes depending on what is being scanned. Multi-headed gamma cameras can provide accelerated acquisition. For example, a dual headed camera can be used with heads spaced 180 degrees apart, allowing two projections to be acquired simultaneously, with each head requiring 180 degrees of rotation. Triple-head cameras with 120 degree spacing are also used.

A computer is then used to apply a tomographic reconstruction algorithm to the multiple projections, yielding a 3-D dataset. This dataset may then be manipulated to show thin slices along any chosen axis of the body, similar to those obtained from other tomographic techniques, such as MRI, CT, and PET.

Figure 4:
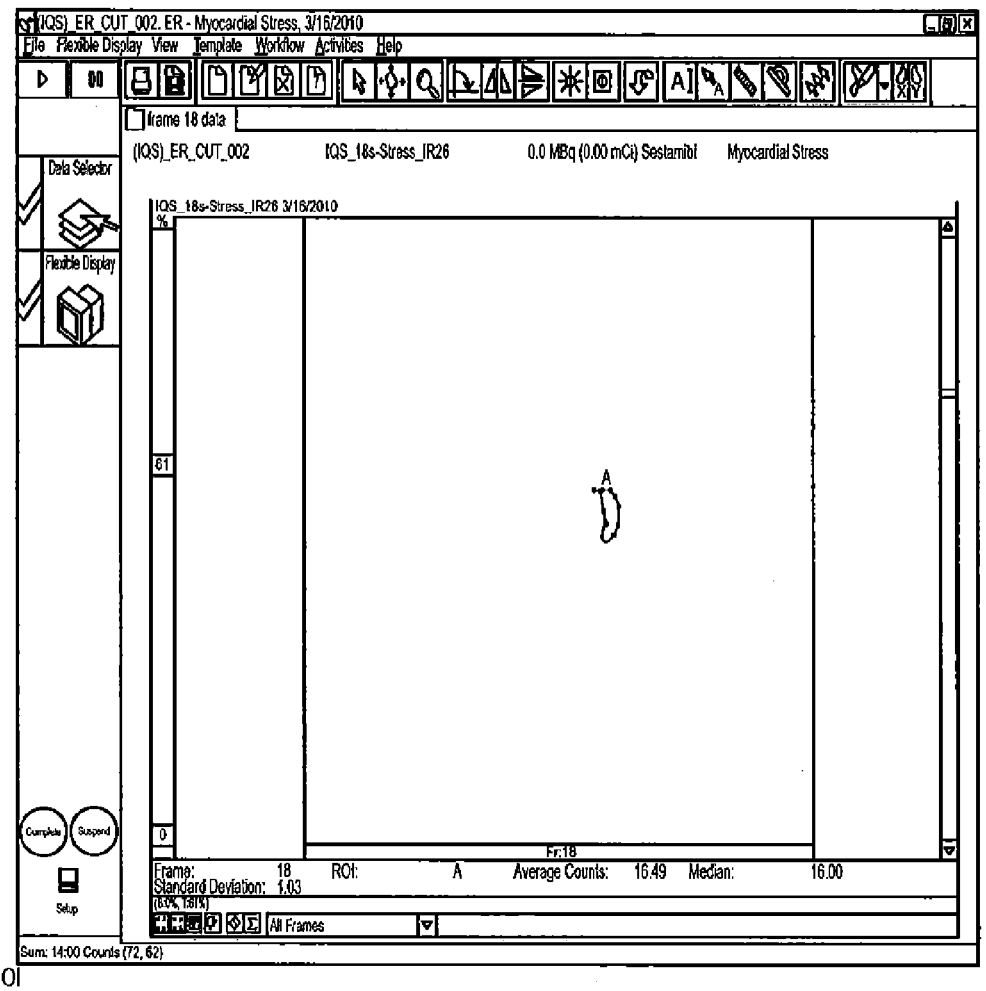
FIG. 4 is a diagram depicting a region of interest for a projection view in accordance with an embodiment of the present invention.

In accordance with an embodiment of the present invention, a specific view is selected from all of the projections. Specifically a view is selected that projects the organ of interest e.g., the heart as an annulus. A region of interest in the annulus of the myocardium in the projection view is selected. A specific shape of the ROI is not required. However, the ROI should preferably be in the lateral wall see FIG. 4. The lateral wall is selected because its typically lower in counts due to attenuation and is also more likely to be affected by disease. An average count density c is determined.

The correlation between injected dose at scan time d(t$_s$) (in mCi) multiplied by the dwell time T$_d$(in s) allows for a relationship between the average counts in that ROI (c). The correlation factor f is defined as the protocol scan efficiency. The protocol efficiency is empirically determined and is influenced by system parameters such as collimator type, number of views, reconstruction type and the like and patient specific parameters such as gender, BMI and the like. The value of c can be determined from equation 1 below.

$$c = f * d(t_s) * T_d \quad (1)$$

where f is the protocol scan efficiency (correlation factor)
d(t$_s$) is the injected dose at scan time and
T$_d$ is the dwell time It is critical to ensure that one defines a base protocol comprising the selection of the SPECT system, collimator, number of views, scan arc, start angle, isotope and acquisition window width and to keep the base protocol unchanged. This then provides for a change of dwell time.

Figure 5:
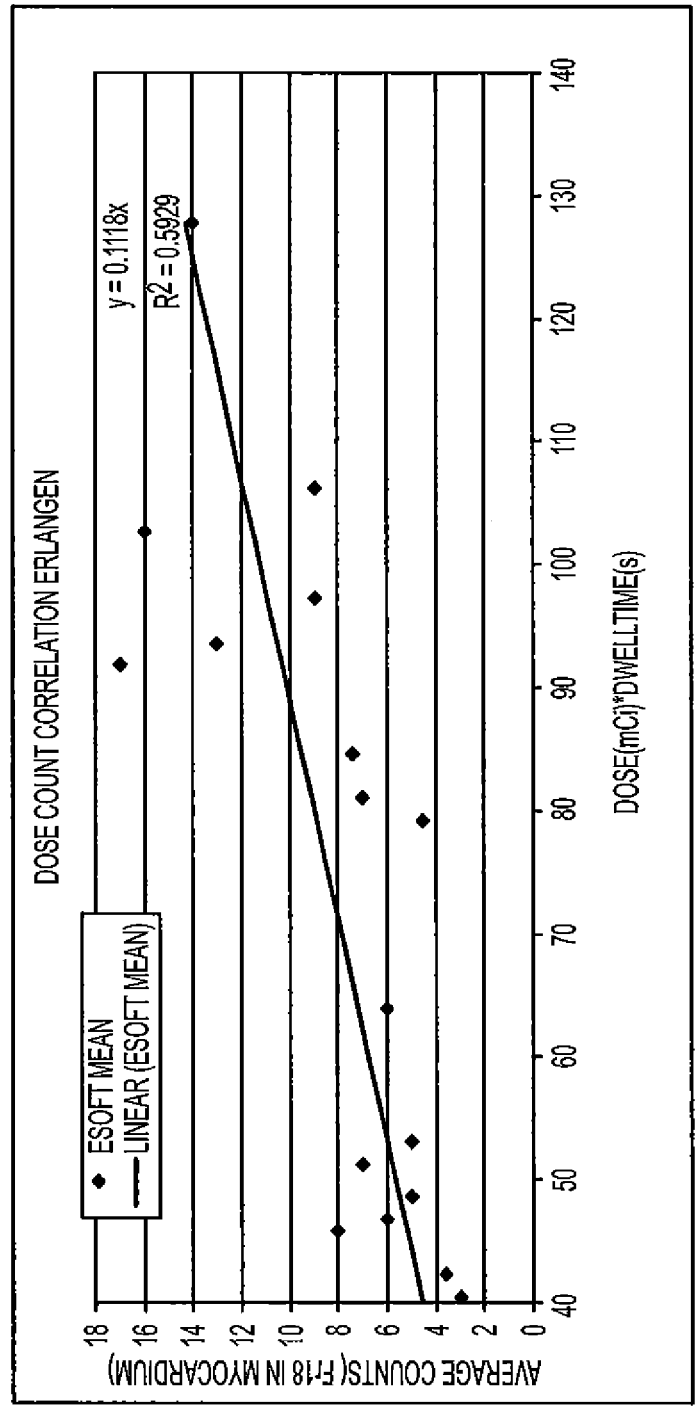
FIG. 5 is a graph depicting a correlation between product of scan efficiency, scan dose and dwell time in accordance with an embodiment of the present invention.

A test data set is used to determine the protocol scan efficiency f based on a specific base protocol. The more clinical data one uses, the more one can stratify the scan efficiency to include more independent variables and improve the prediction of the myocardial. For this example, a constant f=0.1 for a variable collimator and a specified protocol was extracted (See FIG. 5). FIG. 5 shows the average counts on the y axis and dose multiplied by the dwell time on the x axis. FIG. 5 overall shows a correlation between product of scan efficiency, scan dose and dwell time.

The counts in the lateral wall are correlated in order to predict basic image quality in the reconstructed image assuming all other degrading factors are equal. FIG. 6 shows four regimes ("not recommended" poor IQ c<5, "careful" [may require parameter adjustment 4<c<11], "recommended", likely good IQ 11<c<21, "highly recommended", likely very good IQ c>20) which have proven to work well. The actual values are specific to the base protocol, and the exact numbers and thresholds may change and may be adapted depending on the type of reconstruction algorithm used.

The above information can be used to optimize a clinical workflow. The steps below can be used to plan a patient workflow or to adapt to changes in patient scheduling. The injected dose at injection time should be recorded or planned. Next the scan time should be planned. Delay time=Scan time−Injection time should be computed. Next Scan Dose=Injected dose (mCi)*Decay Correction (Isotope T$_{1/2}$, Delay Time) should be computed. A desired operation range e.g., c range should be determined. Then c=f*Scan Dose*dwell time should be computed or the use of look up tables can be used. It should be noted that dwell time restrictions may apply for lower or upper bounds such as: don't lower dwell time below x seconds to avoid breathing artifacts.

Figure 2:
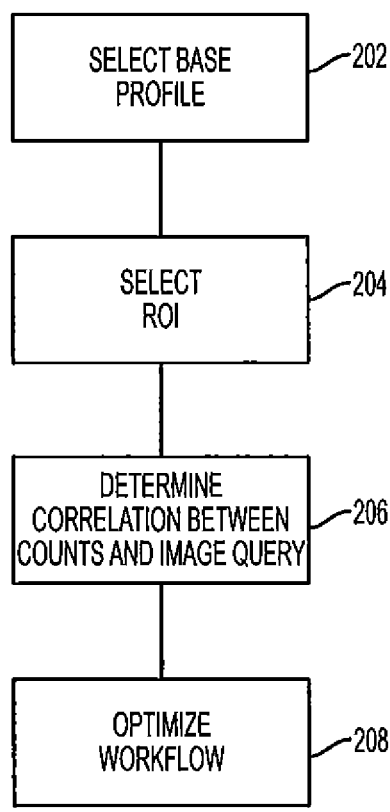
FIG. 2 is a flow chart illustrating a process for optimizing radiation exposure for medical equipment in accordance with an embodiment of the present invention.

FIG. 2 is a flow chart illustrating a process for optimizing radiation exposure for medical equipment in accordance with an embodiment of the present invention. The method 200 is initiated at step 202 where a base profile is selected. This base profile is maintained and includes system and patient parameters such as collimator type, SPECT system, number of views, scan arc, start angle, isotope, acquisition window width, reconstruction type, patient gender, BMI, weight, height, age, and the like.

At step 204, an ROI is selected from the projections. Specifically, a projection that projects the heart as an annulus. The ROI is preferably in the lateral wall of the heart because typically because it's lower in counts due to attenuation and more likely to be affected by disease. An average count density is determined from the ROI. The correlation between the injected dose at scan time multiplied by the dwell time allows for a relationship between the average counts in the ROI. Since the base protocol is unchanged. Only a change in dwell time is allowed.

At step 206, a correlation between the average counts in the ROI is used to predict the image quality in the reconstructed image. At step 208, the information is used to optimize the clinical workflow.

Figure 3:
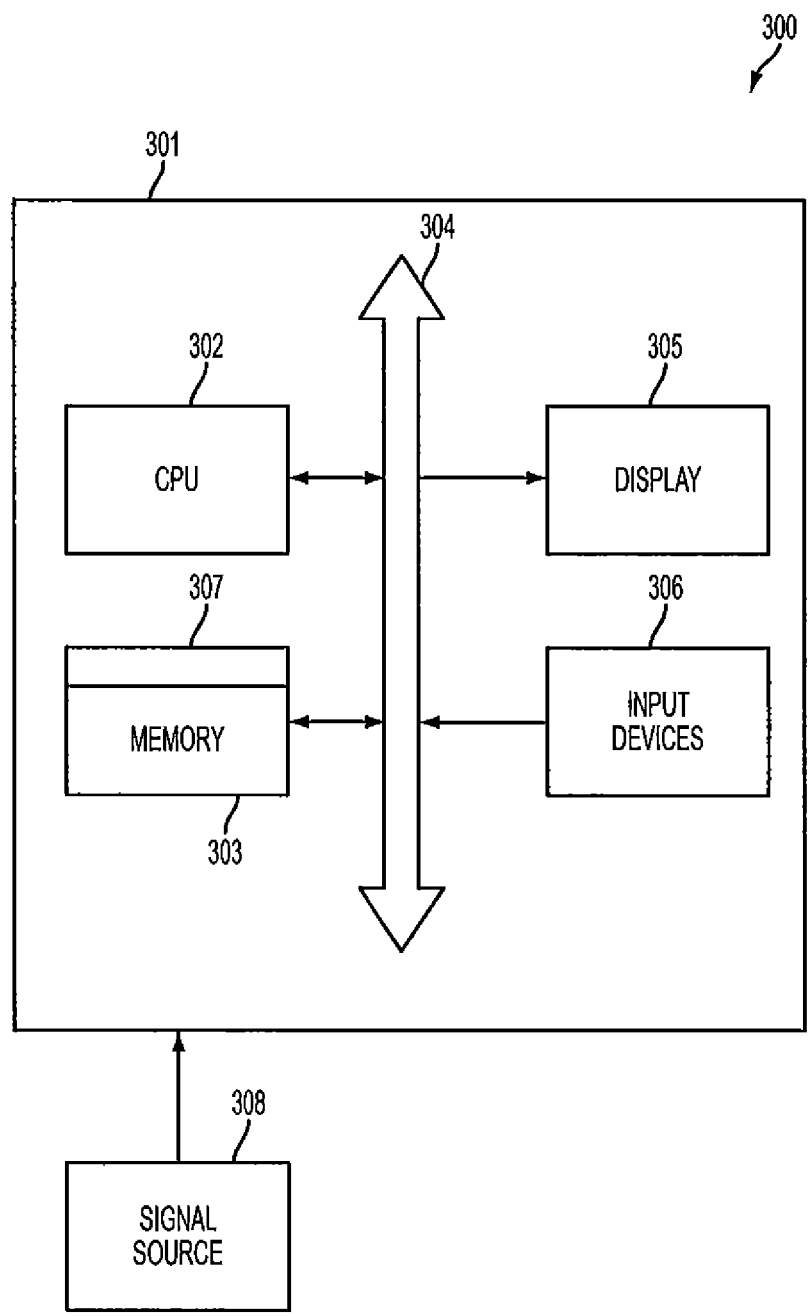
FIG. 3 is a block diagram of a computer for optimizing radiation exposure in accordance with an embodiment of the present invention.

Referring now to FIG. 3, according to an embodiment of the present invention, a computer system 301 for implementing the present invention can comprise, inter alia, a central processing unit (CPU) 302, a memory 303 and an input/output (I/O) interface 304. The computer system 301 is generally coupled through the I/O interface 304 to a display 305 and various input devices 306 such as a mouse and a keyboard. The support circuits can include circuits such as cache, power supplies, clock circuits, and a communication bus. The memory 303 can include random access memory (RAM), read only memory (ROM), disk drive, tape drive, etc., or a combinations thereof. The present invention can be implemented as a routine 307 that is stored in memory 303 and executed by the CPU 302 to process the signal from the signal source 308. As such, the computer system 301 is a general purpose computer system that becomes a specific purpose computer system when executing the routine 307 of the present invention.

The computer system 301 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for optimizing an amount of radiation dose and acquisition time in cardiac Single Photon Emission Computed Tomography (SPECT) imaging, the method comprising:
   providing an organ;
   acquiring images of the organ at projected views;
   selecting a projected view that projects the organ as an annulus;
   selecting a region of interest (ROI) in the projected view, wherein the ROI is in a lateral wall of the organ;
   determining an average count in the ROI; and
   predicts an image quality of a reconstructed image based on the average count.

2. The method of claim 1, further comprising:
   determining the average count using an equation of $$c = f * d(t_s) * T_d$$

where f is a protocol efficiency
   $d(t_s)$ is the injected dose at scan time
   $T_d$ is a dwell time.

3. The method of claim 1, further comprising:
   optimizing a clinical workflow based on a result of the average count.

4. The method of claim 1, further comprising:
   determining a correlation between the average count and scan parameters.

5. The method of claim 1, further comprising:
   establishing a performance envelope based on ranges for the average count.

6. The method of claim 1, further comprising:
   selecting a predetermined amount of system parameters.

7. The method of claim 6, further comprising:
   selecting a predetermined amount of patient parameters.

8. The method of claim 6, wherein the amount of system parameters used is less than an amount of system parameters used in a conventional scan.

9. The method of claim 7, wherein the amount of patient parameters used is less than an amount of patient parameters used in a conventional scan.

10. The method of claim 6, wherein the system parameters comprise at least one of a collimator, number of views, and reconstruction type.

11. The method of claim 7, wherein the patient parameters comprise at least one of a gender type, BMI, weight, and height.

12. The method of claim 1, further comprising:
    selecting a base protocol.

13. The method of claim 12, wherein the base protocol comprises selection of a collimator type, number of views, scan arc, start angle, isotope, acquisition window width and system parameters and SPECT system.

14. The method of claim 12, further comprising:
    maintaining the base protocol.

15. The method of claim 1, wherein the organ comprises a heart.

16. The method of claim 1, further comprising:
    performing a myocardial perfusion test.

17. An apparatus for optimizing an amount of radiation dose and acquisition time in cardiac imaging comprising:
    an input device which accepts commands;
    a display device which displays the image;
    a memory which stores programs;
    a processor which
    acquires images of an organ at projected views;
    selects a projected view that projects the organ as an annulus;
    selects a region of interest (ROI) in the projected view, wherein the ROI is in a lateral wall of the organ;
    determines an average count in the ROI; and
    predicts an image quality of a reconstructed image based on the average count.

18. The apparatus of claim 17, wherein the processor determines the average count using an equation of $$c = f * d(t_s) * T_d$$

where f is a protocol efficiency
    $d(t_s)$ is the injected dose at scan time
    $T_d$ is a dwell time.

19. The apparatus of claim 17, wherein the apparatus comprises a Single Photon Emission Computed Tomography (SPECT) or a SPECT/CT.

20. A computer program product, residing on a computer readable medium, comprising computer executable instructions for optimizing an amount of radiation dose and acquisition time in cardiac imaging causing a computer to perform the following functions comprising:
    acquiring images of an organ at projected views;
    selecting a projected view that projects the organ as an annulus;
    selecting a region of interest (ROI) in the projected view, wherein the ROI is in a lateral wall of the organ;
    determining an average count in the ROI; and
    predicting an image quality of a reconstructed image based on the average count.

* * * * *